US007838226B2

(12) United States Patent
Kamahori et al.

(10) Patent No.: US 7,838,226 B2
(45) Date of Patent: Nov. 23, 2010

(54) DEOXYRIBONUCLEIC ACID MEASURING APPARATUS AND METHOD OF MEASURING DEOXYRIBONUCLEIC ACID

(75) Inventors: Masao Kamahori, Kokubunji (JP); Yu Ishige, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 355 days.

(21) Appl. No.: 11/491,128

(22) Filed: Jul. 24, 2006

(65) Prior Publication Data
US 2007/0059741 A1 Mar. 15, 2007

(30) Foreign Application Priority Data
Sep. 15, 2005 (JP) ............... 2005-269029
Apr. 28, 2006 (JP) ............... 2006-126262

(51) Int. Cl.
C12Q 1/68 (2006.01)
C12P 19/34 (2006.01)
C12M 1/00 (2006.01)
G01N 15/06 (2006.01)

(52) U.S. Cl. ............. 435/6; 435/91.1; 435/91.2; 435/283.1; 422/82.01; 536/23.1

(58) Field of Classification Search ............... None
See application file for complete search history.

(56) References Cited

U.S. PATENT DOCUMENTS

| 4,437,969 | A | * | 3/1984 | Covington et al. ......... 257/253 |
| 6,051,380 | A | * | 4/2000 | Sosnowski et al. ......... 435/6 |
| 6,295,630 | B1 | * | 9/2001 | Tamegaya ................ 716/4 |
| 6,828,100 | B1 | * | 12/2004 | Ronaghi .................. 435/6 |
| 6,916,614 | B1 | * | 7/2005 | Takenaka et al. .......... 435/6 |
| 2004/0152091 | A1 | * | 8/2004 | Paulus et al. ............. 435/6 |
| 2005/0106587 | A1 | * | 5/2005 | Klapproth et al. ......... 435/6 |

FOREIGN PATENT DOCUMENTS

JP 2005-077210 8/2003

(Continued)

OTHER PUBLICATIONS

Sakata et al "Direct Detection of Single Nucleotide Polymorphism Using Genetic Field Effect Transistor" Microprocesses and Nanotechnology Conference, Oct. 27, 2004: 226-227.*

(Continued)

Primary Examiner—B J Forman
(74) Attorney, Agent, or Firm—Stites & Harbison, PLLC; Juan Carlos A. Marquez, Esq.

(57) ABSTRACT

With an insulated gate field effect transistor in which deoxyribonucleic acid (DNA) probes are immobilized on a gold electrode, extension reaction on the gold electrode is performed with DNA polymerase to directly measure an increased amount of a phosphate group caused by the extension reaction, that is, negative charge, by means of a current change between a source and a drain of the insulated gate field effect transistor. Thus, presence/absence of hybridization of target DNAs with the DNA probes, and presence/absence of the extension reaction are detected. Optimum immobilization density of the DNA probes on the gold electrode is set at $4 \times 10^{12}$ molecules/cm$^2$. To reduce surface potential fluctuation caused by external variation (influences of foreign substances), which is a problem when using the gold electrode in a solution, a high-frequency voltage equal to or above 1 kHz is applied between the gold electrode and a reference electrode by a power source.

14 Claims, 11 Drawing Sheets

FOREIGN PATENT DOCUMENTS

| | | |
|---|---|---|
| WO | WO 97/39145 | 4/1997 |
| WO | WO 98/13523 | 9/1997 |
| WO | WO 98/28440 | 12/1997 |

OTHER PUBLICATIONS

Sakata et al "DNA sequencing using genetic field effect transistor" IEEE, Jun. 2005: 1676-1679.*

Yasuhito Ebara et al., "In Situ Surface-Detecting Technique by Using a Quartz-Crystal Microbalance. Interaction Behaviors of Proteins onto a Phospholipid Monolayer at the Air-Water Interface", Langmuir, vol. 9, No. 2, 1993, pp. 574-576.

Kenichi Niikura et al., "Direct Monitoring of DNA Polymerase Reactions on a Quartz-Crystal Microbalance", J. Am. Chem. Soc., vol. 120, No. 33 (1998), pp. 8537-8538.

K. Keiji Kanazawa et al., "The Oscillation Frequency of a Quartz Resonator in Contact with a Liquid", Analytic Chimica Acta, 175 (1985), pp. 99-105.

* cited by examiner 112 113 111

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
cacactcaca gttttcactt                                              20

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
tgggcgagta cgggctgcag gcatacacta aagtgaaaac tgtgagtgtg             50

<210> SEQ ID NO 3
<211> LENGTH: 30
<212> TYPE: DNA
<213> ORGANISM: Artificial Sequence -continued

```
<220> FEATURE:
<223> OTHER INFORMATION: Description of Artificial Sequence:Synthetic
      DNA

<400> SEQUENCE: 3
gcatacacta aagtgaaaac tgtgagtgtg                                    30

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
cgggctgcag gcatacacta aagtgaaaac tgtgagtgtg                         40

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
tgtaaaacga cggccagt                                                 18

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
atcacatacg                                                          10
```

US 7,838,226 B2

DEOXYRIBONUCLEIC ACID MEASURING APPARATUS AND METHOD OF MEASURING DEOXYRIBONUCLEIC ACID

CLAIM OF PRIORITY

The present application claims priority from Japanese applications JP 2005-269029 filed on Sep. 15, 2005 and JP 2006-126262 filed on Apr. 28, 2006, the contents of which are hereby incorporated by reference into this application.

BACKGROUND OF THE INVENTION

1. Field of the Invention

The present invention relates to a deoxyribonucleic acid (DNA) sensor for measuring DNAs without modification thereof, and to a method of measuring the DNAs by using the sensor.

2. Description of the Related Art

Today, a basic principle of DNA chips which are widely used for analyzing functions of genes and gene expressions is a fluorescence detection method. Accordingly, a laser light source and a complicated optical system are required. As a result, a measurement system is large and high-priced. DNA probes used in this case are required to be labeled by using a fluorescent substance, and moreover, a cleaning operation (bound free separation; BF separation) is needed for removing free fluorescence-labeled DNA probes after binding fluorescence-labeled DNA probes to target DNAs (i.e., hybridization).

Methods of measuring the DNAs without modification thereof and without requiring fluorescent substances have been developed in recent years. Such methods, for instance, include: the quartz crystal microbalance (QCM) method configured to immobilize DNA probes on a surface of a quartz resonator and to measure a resonance frequency of the quartz resonator which changes before and after hybridization with target DNAs; and the surface plasmon resonance (SPR) method configured to measure a state change of a liquid on a surface of a sensor before hybridization of target DNAs with DNA probes, which are immobilized on the surface of the sensor by use of the surface plasmon resonance. The QCM measurement basic principle is reduction in the oscillation frequency (frequency variation) caused by adsorption of a substance to an electrode of the quartz resonator, in which a relationship between the oscillation frequency change and a mass of the adsorbed substance is expressed by the following formula called the Sauerbrey formula:

$$\Delta F = -\frac{2F_0^2}{A(\mu_Q \rho_Q)^{1/2}} \Delta m$$

where, $\Delta m$ denotes an amount of mass change; $F_0$ denotes fundamental oscillation frequency; $\Delta F$ denotes an amount of change in fundamental oscillation frequency; $A$ denotes an area of an electrode; $\mu_Q$ denotes shear modulus of quartz; and $\rho_Q$ denotes density of quartz.

The change in the mass of the quartz resonator on the electrode is proportional to the change in the oscillation frequency. For example, it is confirmed that, when the quartz resonator having a fundamental oscillation frequency $F_0$ (Hz) of 27 MHz is used in the air, a 1 Hz oscillation frequency is reduced by adsorption of a substance in an amount of 0.62 ng to each 1 cm² of an electrode. In the case of single base extension where a single base is added, assuming that immobilization density of DNAs is $4 \times 10^{12}$ molecules/cm² and that a change in the molecular mass per a single base extension is approximately 300, extension of a single base causes a change in the mass by $2.0 \times 10^{-9}$ g/cm². This value is equivalent to an amount of change in frequency by about 3 Hz. However, the single base extension comes under the influence of a change in the viscosity of a solvent under the condition in which the quartz resonator is actually used in a liquid (Anal. Chim. Acta 175 (1985) 99-105). The influence of the change in the viscosity of the solvent is expressed by the following formula:

$$\Delta F = -F_0^{2/3} (\rho_n \eta_L / \pi \rho_Q \eta_Q)^{1/2}$$

where $\rho_L$ denotes density of solvent; $\eta_L$ denotes viscosity of solvent; $\rho_Q$ denotes density of quartz; and $\eta_Q$ denotes shear modulus of quartz.

This indicates that actual measurement is influenced by a change in the temperature in addition to a pulsating flow in introducing a sample and to a change in solution composition. For example, as for the influence of the temperature change in the case of water, the change in the viscosity is dominant. In this case, the change ratio in the viscosity is 2%/° C., and the change in the frequency is approximately 1000 Hz/° C. This value means that a change in the temperature of 1° C. is equivalent to a change in the mass of $6.0 \times 10^{-7}$ g/cm². For this reason, the QCM method requires a temperature-controlled bath and a liquid pumping-system, which are highly accurate, in order to reduce these influences. As a result, an apparatus therefor is large-scaled and complicated. In the measurement where the temperature is actually controlled, frequency fluctuations range from 16 Hz to 24 Hz approximately, and the minimum limit of detection for the change in the mass ranges from $1.0 \times 10^{-8}$ to $1.5 \times 10^{-8}$ g/cm² (Langmuir 9, (1993) 574-576pp., J. Am. Chem. Soc. 120, (1998) 8537-8538). As described above, the QCM method is sensitive to the temperature change and has a difficulty for measurement of the change in the mass of $2.0 \times 10^{-9}$ g/cm² in the case of a single base extension reaction. Similarly, the SPR method is influenced by the temperature change in addition to the pulsating flow in introducing the sample and to the change in the solution composition.

On the other hand, some methods which are paid attention to as small-size and simple methods include the pyrosequencing method and a filed effect transistor (FET) sensor. The pyrosequencing method is configured to hybridize target DNAs with DNA probes, convert pyrophosphate generated in a complementary strand extension reaction to adenosine triphosphate (ATP), cause this ATP to emit light by use of a luciferin-luciferase luminescence system, identify a substrate (deoxyribonucleoside triphosphate) incorporated in the complementary strand extension reaction by detecting this bioluminescence, and then, determine a base sequence sequentially from the adjacent regions of a primer (Anal. Chem. Acta. 175, (1985) 99-105 pp., Japanese Patent Translation Publication No. 2001-506864, and Japanese Patent Publication No. 3510272). The FET sensor is configured to immobilize DNA probes on a gate insulating layer formed on a space between a source and a drain, and to detect, as a change in a current value between the source and the drain, surface potential on an insulating film generated by hybridization of the DNA probes with target DNAs (Japanese Patent Translation Publication No. 2001-511245). In these methods, the detecting method by using the bioluminescence is a promising method as a detecting method capable of detecting the presence or absence of hybridization of the target DNAs with the DNA probes without using a fluorescent substance label or BF separation.

The above-described pyrosequencing method using the bioluminescence method is configured of three enzyme reaction processes including an extension reaction by DNA polymerase, a reaction to convert pyrophosphate generated by the extension reaction to ATP (for example, ATP sulfurylase), and a reaction to cause light emission with a luciferin-luciferase luminescence system by utilizing ATP generated by an ATP conversion enzyme. Accordingly, the respective enzymes need different reagents such as substrates. Moreover, the enzyme reactions used herein have respectively different optimal reaction conditions, and thereby. it is necessary to adjust the reaction conditions in order for the respective enzymes to act as much as possible. In addition, in deoxyribonucleoside triphosphate selected from a group consisting of dATP (deoxyadenosine triphosphate), dCTP (deoxycytidine triphosphate), dGTP (deoxyguanosine triphosphate) and dTTP (deoxythymidine triphosphate) used for the extension reaction, the dATP is a pseudosubstrate (i.e., a luminescent substance) of a luciferin-luciferase reaction and is therefore a noise source. Accordingly, it is necessary to use deoxyadenosine α-thiotriphosphate (dATPαS) as an analog (Japanese Patent Publication No. 3510272). The dATPαS is more expensive than the dATP, while the dATPαS has problems of poor reactivity as a DNA polymerase substrate, and of poor thermostability to cause the decomposition thereof easily. Meanwhile, since the deoxyribonucleoside triphosphate contains the pyrophosphate which is the substrate of this reaction, it is necessary to perform a complicated process to decompose the pyrophosphate by use of an enzyme such as pyrophosphatase. In order to perform processing of numerous samples at the same time, it is necessary to minimize a reaction tank and to perform a two-dimensional array at high density. In this case, there are problems: of deterioration in sensitivity owing to reduction in the amount of light emission with the reaction tank downsizing; and of crosstalk in which light emission is leaked within the reaction tanks with the density in the two-dimensional array increasing.

Meanwhile, in principle, the FET sensor can detect, as a potential change, an increased amount of a phosphate group added by the extension reaction of the DNA probes immobilized on the gate insulating layer formed on a space between the source and the drain. As compared to luminescence detection, the FET sensor has an advantage of requiring fewer reagents (such as enzymes or substrates) used therefor. Nevertheless, in the conventional technique, the DNA probes are immobilized on the gate insulating layer in the following manner: an amino group is introduced by chemically modifying the surface of the gate insulating film by use of aminopropylsilane, polylysine or the like; and the DNA probes each having an end which is chemically modified with the amino group by use of glutaraldehyde or phenylenediisocyanate. Therefore, this technique requires the complicated preprocessing. In recent years, an extended gate FET has been disclosed (Japanese Patent Publication No. 2005-77210), and in the extended gate FET, a gold electrode for DNA probe immobilization is connected to a gate of an insulated gate field effect transistor with a conductive wire. By using the gold electrode in a sensing area which is a DNA immobilization area, the specific binding between gold and a thiol can be applied. Accordingly, by using the specific binding, the DNA probes each including alkanethiol as a linker can be easily immobilized to the gold electrode. However, the DNA probe immobilization form suitable for the extended gate FET sensor and the usage thereof have not yet been studied in detail.

In particular, a relation between hybridization efficiency and immobilization density of the DNA probes, the relation having large influence on detection sensitivity, and a method of reducing an influence of a disturbance factor in a solution due to foreign substances and the like have not been clarified. In addition, a suitable array of sensors and the like for simultaneously processing numerous samples have not also been made clear.

SUMMARY OF THE INVENTION

In the present invention, with an extended gate FET sensor in which DNA probes are immobilized on a gold electrode, an extension reaction on the gold electrode is performed with DNA polymerase. Thereafter, an increase in acid groups each having a single phosphate group added to each of the DNA probes by the extension reaction, i.e., an increase in negative charge of the DNA probes immobilized on a solid phase, is directly measured by means of the extended gate FET sensor, instead of indirectly measuring pyrophosphate which is a product of the extension reaction. The extension reaction on the gold electrode can use an enzyme used in a usual sequencing method. Needless to say, it is also possible to use DNA polymerase used in the pyrosequencing method involving stepwise reactions. Examples of the DNA polymerase include T7 polymerase, Klenow, Sequenase Ver. 2.0, and the like, and it is possible to arbitrarily use any of the suitable polymerase. Here, a substrate used therefor is one of deoxyribonucleoside triphosphate selected from a group consisting of dATP, dCTP, dGTP and dTTP. Unlike the pyrosequencing method, it is not necessary to use the dATPαS as the analog instead of the dATP which is a noise source. When performing DNA sequencing, each type of the deoxyribonucleoside triphosphate, which is the substrate for the extension reaction, is added one by one, and then the presence or absence of the extension reaction is determined based on a drain current value changed before and after the addition of the deoxyribonucleoside triphosphate. To be more precise, it is possible to determine a sequence by repeating a cycle of rinsing off and removing the excessive deoxyribonucleoside triphosphate after measuring the presence or absence of the extension reaction, and then of performing the next extension reaction after adding another deoxyribonucleoside triphosphate. To remove the excessive deoxyribonucleoside triphosphate, apyrase, which is a substrate decomposing enzyme, may be mixed with a reactive solution, as the case of a pyrosequencing reaction.

Further enhancement of the measurement sensitivity may be achieved by a use of a derivative, as the substrate, in which an additional portion carrying negative charge is bound to a side chain of a constituent base of the deoxyribonucleoside triphosphate. For example, a derivative, in which either a phosphoric acid or a polyphosphoric acid is bound to an amino group of a base with a carbon-chain linker interposed in between, may be used.

In the case of processing numerous samples at the same time, the gold electrode and either a reference electrode or a pseudo-reference electrode may be disposed on the same plane so as to face one another.

DNA probe immobilization on the gold electrode can be realized by a simple operation of dripping or spotting a DNA probe solution to the surface of the gold electrode, the DNA probe solution containing alkanethiol in an end of each of the DNA probes. Immobilization density of the DNA probes on the gold electrode may be optimized in order to realize enhancement of hybridization efficiency on the gold electrode, the enhancement having a large influence on detection sensitivity. In order to optimize the immobilization density of the DNA probes, it is possible to use a DNA immobilization solution containing the DNA probes and a compound with a certain molecules number ratio. Here, the DNA probes are bound to the linkers each having a reactive group to be bound to the gold electrode, while the compound contains only the linkers each having the reactive group to be bound to the gold electrode. Use of the DNA immobilization solution causes the DNA probes to be immobilized under a competitive reaction with the compound containing only the linkers, whereby the immobilization density of the DNA probes can be optimized. In this way, it is possible to maintain the optimal hybridization efficiency. In general, the immobilization density of alkanethiol is $4.6 \times 10^{14}$ molecules/cm$^2$. Meanwhile, since a diameter of double-stranded DNA is approximately 2.4 nm, it is preferable to set the immobilization density of the DNA probes equal to or below $4 \times 10^{12}$ molecules/cm$^2$ in order to efficiently perform the hybridization. Considering the measurement sensitivity, the immobilization density of the DNA probes is set preferably to be in a range from $4 \times 10^{10}$ molecules/cm$^2$ to $4 \times 10^{12}$ molecules/cm$^2$. By satisfying this condition, it is possible to maintain both the optimal hybridization efficiency and a shielding effect on the surface of the gold electrode at the same time. The DNA immobilization solution used therefor may contain the DNA probes and the alkanethiol with molecules number ratios from 1:2 to 1:100, concentration of the alkanethiol being equal to or above 0.5 mM. The DNA probes stated herein are those hybridized with target DNAs, and are single-stranded, for example, DNA, RNA, PNA or the like.

Usually, alkanethiol including an alkyl group having three or more carbon chains is used as the compound containing only the linker. The alkanethiol usable therein has an amino group, a hydroxyl group or a carboxyl group at the end of carbon chain. In the case of DNA probe immobilization, since the DNA is charged negatively, DNA fragments lie down on the surface, due to an interaction in using the alkanethiol containing the amino group, and thereby measurement stability (stabilization time and fluctuation of measurement value) is deteriorated. Therefore, it is better to use the alkanethiol containing the hydroxyl group or the carboxyl group as the end group. The alkanethiol used therefor may be, for example, mercaptoethanol, 6-hydroxy-1-hexanethiol, 8-hydroxy-1-octanethiol, 11-hydroxy-1-undecanethiol and the like each containing the hydroxyl group as the end group. However, there is no problem in using the alkanethiol containing any of the amino group, the carboxyl group, and the hydroxyl group as the end group according to electric charge in a measurement object.

Concerning surface potential fluctuation (i.e. drift) attributable to external variation (influences of foreign substances) which becomes problematic when using the gold electrode in a solution, it is possible to reduce the influences by applying a high-frequency voltage equal to or above 1 kHz between the gold electrode and the reference electrode. Note that, the high-frequency voltage application does not cause disconnection between the DNA probes and the measurement objects. Moreover, use of the gold electrode prevents a reaction on the surface of the electrode in the solution from occurring.

In the present invention, by use of an extended gate FET sensor in which DNA probes are immobilized to a gold electrode, it is made possible to perform an extension reaction using DNA polymerase on a gold electrode, and thereby, to totally electronically measure a product of the extension reaction, directly by the extended gate FET sensor without the modification of the product and without requiring any fluorescent substances. Concerning the substrate used therein, it is not necessary to use the expensive and unstable dATPαS, as the analog, instead of the dATP unlike the pyrosequencing method. In addition, it is not necessary to perform a process for removing a pyrophosphoric acid contained in the deoxyribonucleoside triphosphate (dATP, dCTP, dGTP or dTTP).

Moreover, in the case of the pyrosequencing reaction, since the pyrosequencing reaction requires numerous reagents (enzymes, substrates and the like), an excess of the deoxyribonucleoside triphosphate is removed in a manner that the reactive solution is mixed with apyrase which is a substrate decomposing enzyme. By contrast, the enzyme used in the present invention is only polymerase. Therefore, it is possible to clean the substrate to remove the excess thereof, immediately after one base extension reaction is completed. In this way, the present invention makes it possible to accelerate a reaction cycle to obtain an effect to reduce the time for DNA sequencing.

By using, as the substrate used for the extension reaction, a derivative in which an additional portion having a negative charge is bound to a side chain of a constituent base of the deoxyribonucleoside triphosphate, it is possible to increase a potential change, accompanying the extension reaction, on the surface of the gold electrode. For example, in the case of using a derivative in which phosphoric acid or polyphosphoric acid is bound to an amino group in the base with a carbon-chain linker interposed in between, the negative charge is increased by twice to three times. Accordingly, the potential change, accompanying the extension reaction, on the surface of the gold electrode is also increased by two to three times, thus enabling highly sensitive measurement.

When the potential measurement is performed by using a single reference electrode for numerous gold electrodes in order to process numerous samples at the same time, the measurement is susceptible to an influence of a potential change of adjacent gold electrodes or an influence of a difference in the applied potential caused by a difference in the distances between the respective gold electrodes and the reference electrode. However, it is possible to measure numerous samples at the same time while avoiding the influences of the potential changes on the adjacent gold electrodes, by means of disposing the gold electrodes and either reference electrodes or pseudo-reference electrodes on the same plane so as to face one another. In this way, it is possible to eliminate a problem of crosstalk accompanying a high density growth in the two-dimensional array for processing the numerous samples at the same time.

It is possible to easily control the immobilization density (equal to or below $4 \times 10^{12}$ molecules/cm$^2$) of the DNA probes on the gold electrode to an efficient level for hybridization, by use of a DNA immobilization solution containing the DNA probes and alkanethiol with molecule number ratios from 1:2 to 1:100. In this way, it is possible to fabricate a DNA immobilized FET sensor which maintains the optimal hybridization efficiency. Thus, although there is a problem of an influence of ions in the solution on the surface of the gold electrode of the extended gate FET sensor, the influence can be easily eliminated by controlling the immobilization density of the alkanethiol in the DNA immobilization solution to be equal to or above $4 \times 10^{14}$ molecules/cm$^2$, thus maintaining a shielding effect on the surface of the gold electrode.

Moreover, concerning surface potential fluctuation (i.e. drift) attributable to external variation (influences of foreign substances existing in the solution) which causes a problem at the time of measurement, it is possible to reduce the influence by applying a high-frequency voltage between the gold electrode and the reference electrode.

BRIEF DESCRIPTION OF THE DRAWINGS

FIG. 4A is a graph showing a measurement result of an element not subjected to a light-shielding measure and FIG. 4B is a graph showing a measurement result of an element subjected to the light-shielding measure.

FIGS. 6A to 6C are views showing an operation flow of a method of immobilization DNA probes to a gold electrode, in which FIG. 6A is a schematic drawing of DNA immobilization solution, FIG. 6B is a view showing a state of controlled immobilization density of the DNA probes, and FIG. 6C is a view showing a state of performing hybridization by use of the DNA probes with the controlled immobilization density.

FIG. 10A shows a derivative to which one phosphate group is bound and FIG. 10B shows a derivative to which two phosphate groups are bound.

DETAILED DESCRIPTION OF THE PREFERRED EMBODIMENTS

Embodiments of the present invention will be described below with reference to the accompanying drawings.

Figure 1:
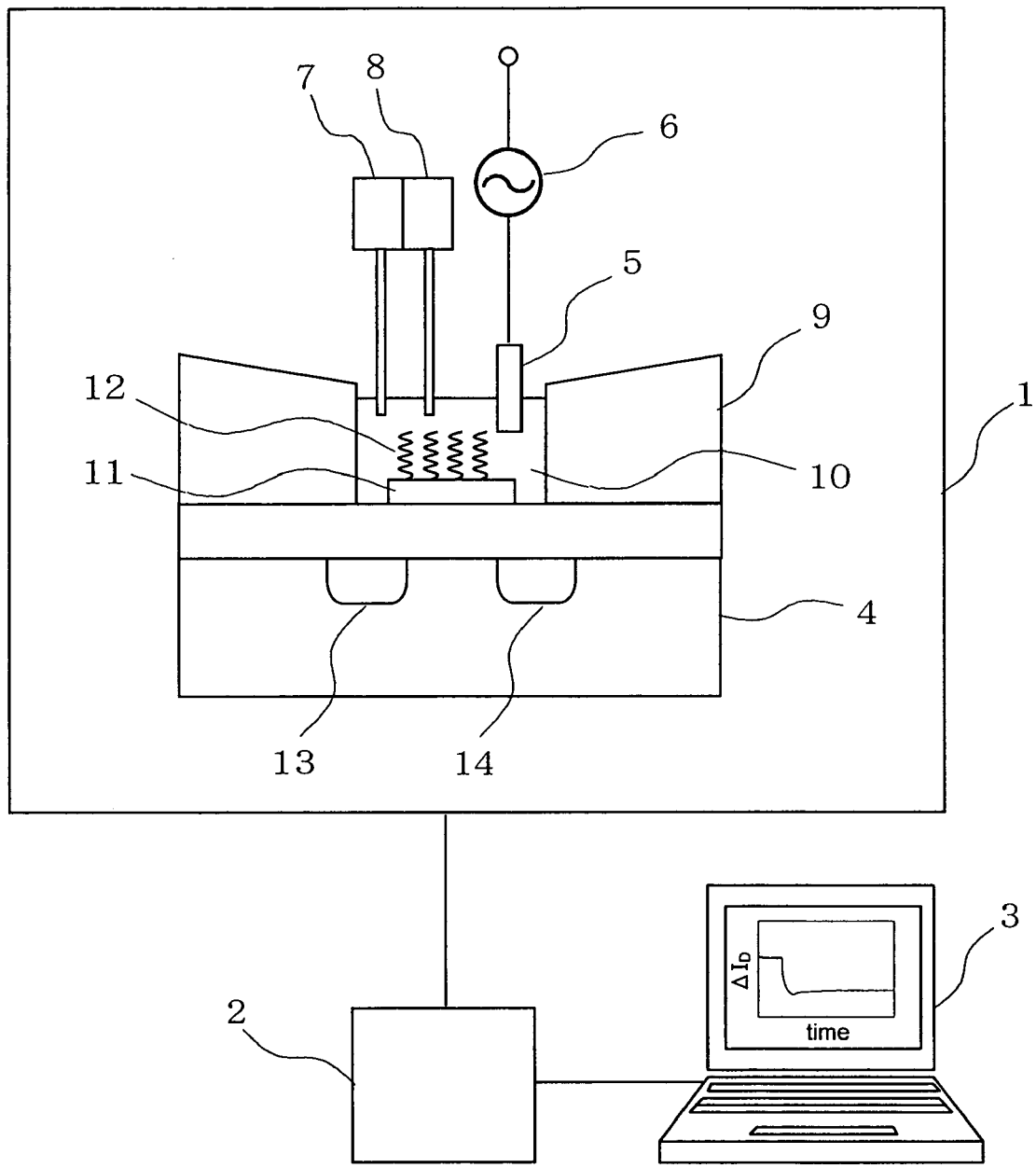
FIG. 1 is a block diagram showing a deoxyribonucleic acid (DNA) measuring apparatus according to an embodiment of the present invention.

FIG. 1 is a block diagram showing a deoxyribonucleoside acid (DNA) measuring apparatus to which a DNA immobilized field effect transistor (FET) sensor according to a first embodiment of the present invention is applied. A measuring system of this embodiment includes a measuring unit 1, a signal processing circuit 2, and a data processing device 3. The measuring unit 1 incorporates an insulated gate field effect transistor 4, a reference electrode 5, a power source 6 for applying a high-frequency voltage to the reference electrode 5, a target DNA solution injector 7, a substance solution injector 8, and a measuring cell 9. A gold electrode 11 formed on the insulated gate field effect transistor 4, DNA probes 12 immobilized onto a surface of the gold electrode 11, and the reference electrode 5 are disposed in a reactive solution 10 inside the measuring cell 9.

A measurement procedure is as follows. In the beginning, target DNA solution is injected into the reactive solution 10 inside the measuring cell 9 with the target DNA solution injector 7, thereby hybridizing the target DNAs with the DNA probes 12. After a certain period of time, a substrate solution is injected into the reactive solution 10 with the substrate solution injector 8 to cause an extension reaction. Here, the reactive solution 10 in advance contains enzymes and other reagents necessary for the extension reaction other than the substrate. In the measurement, a current change between a source 13 and a drain 14 in the insulated gate field effect transistor 4 is monitored in real time and recorded by use of the signal processing circuit 2 and the data processing device 3. Upon occurrence of hybridization of the target DNAs with the DNA probes 12 and the extension reaction, a surface condition of the gold electrode changes, and thereby, potential of the surface thereof changes as well. Accordingly, it is possible to detect the presence or absence of the hybridization of the target DNAs with the DNA probes 12 and the extension reaction by measuring the change in the current value between the source 13 and the drain 14 before and after addition of the target DNA solution and the substrate solution. In the course of the measurement, a high-frequency voltage is applied from the power source 6 to the reference electrode 5 in order to reduce influences of fluctuations in an outside of the measurement.

A syringe pump or a pressure-driven solution feeding device can be used for the target DNA solution injector 7 or the substrate solution injector 8. Both of the syringe pump and the pressure-driven solution feeding device are applicable when a injected volume is equal to or above 1 μL. However, when the injected volume is equal to or below 1 μL, it is preferable to use the pressure-driven solution feeding device in which a capillary is used for a resistance tube. For example, when the injected volume is 0.2 μL, it is possible to perform an accurate injection under conditions of 2 atm pressure and a pressure time period of 2 seconds by use of a flow-rate controllable capillary having an inside diameter of 25 μm and a length of 20 mm. Although the single substrate solution injector 8 is used in this embodiment, it is also possible to perform a sequence by using four substrate solution injectors for four types of deoxyribonucleoside triphosphate. In this case, in order to remove the excessive unreacted deoxyribonucleoside triphosphate in the reactive solution 10 after the extension reactions, the solution thereof may be removed and rinsed off. To be more precise, after a certain period of time since a certain type of substrate is injected, the reactive solution containing the excessive unreacted deoxyribonucleoside triphosphate may be removed and rinsed off. Thereafter, a process of adding a new reactive solution may be added, and then, the cycle of sequentially adding all the four types of deoxyribonucleoside triphosphate for the extension reactions may be repeated. Alternatively, it is also possible to mix apyrase which is a decomposition enzyme in advance for decomposing the excessive unreacted deoxyribonucleoside triphosphate. This arrangement has an advantage of curtailing the cleaning process. However, the total cycle time is extended because the decomposition reaction requires about one minute each time.

Each of the DNA probes 12 is any of single-stranded DNA, RNA, PNA and the like, and has an alkanethiol linker at an end bound to the gold electrode 11. The reference electrode 5 provides potential serving as a standard in order to stably measure the potential change caused by an equilibrium reaction or a chemical reaction, both of which occur on the surface of the gold electrode 11 in the reactive solution 10. As for the reference electrode, usually, a silver/silver chloride electrode or a calomel electrode, in which saturated potassium chloride is used as an inner solution, is used. However, when a reagent solution for measurement has a constant composition, it is also possible to use only the silver/silver chloride electrode as a pseudo-electrode.

Figure 2:
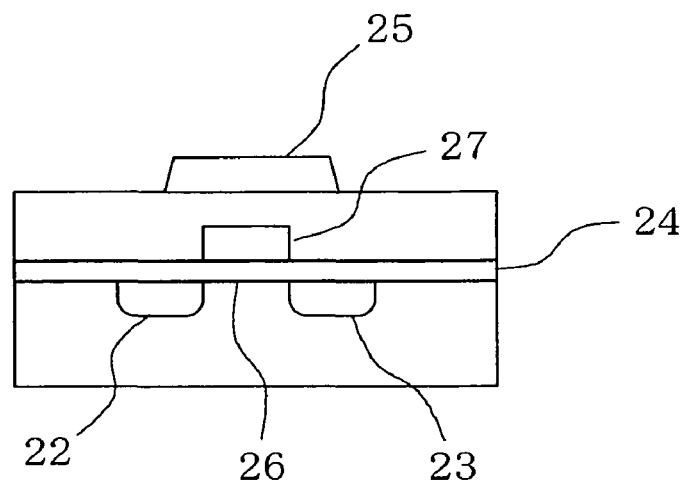
FIG. 2A is a cross sectional view and FIG. 2B is a plain view showing an example of a structure of an insulated gate field effect transistor according to an example of the embodiment of the present invention.
Figure 2:
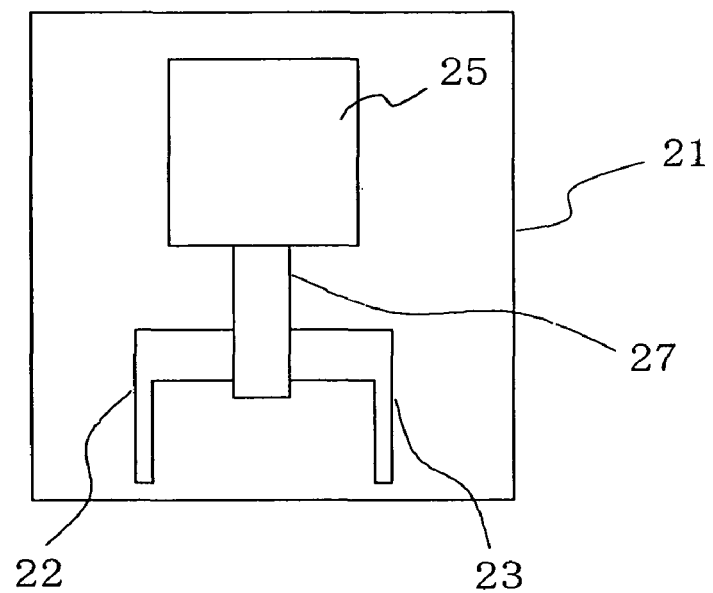

FIGS. 2A and 2B are views showing a structure of the insulated gate field effect transistor used for the DNA measuring apparatus of a first example of this embodiment. Here, FIG. 2A shows a cross-sectional structure and FIG. 2B shows a plane structure. In an insulated gate field effect transistor 21, a source 22, a drain 23, and a gate insulator 24 are formed on a surface of a silicon substrate, while a gold electrode 25 is also provided thereon. The gold electrode 25 for immobilizing DNA probes is connected to a gate 26 of the insulated gate field effect transistor with a conductive wire 27 interposed in between. Preferably, the insulated gate field effect transistor is a metal-oxide-semiconductor field effect transistor (FET) in which a silicon oxide is used as an insulating film. However, it is also possible to use a thin-fill transistor (TFT). By adopting this structure, it is possible to form the gold electrode 25 for immobilizing the DNA probes in an arbitrary place and in an arbitrary size. Moreover, in the case of fabricating various sensor chips used for different measuring objects, it is not necessary to fabricate the chips one by one. Instead, it is possible to fabricate the constituents other than the electrode on which the DNA probe is immobilized in common with the conventional semiconductor processes, and at last step, to fabricate the electrode for a measurement object and to immobilize the probe for the measurement object. In this way, it is possible to widely reduce the manufacturing costs. Meanwhile, the gold electrode for DNA probe immobilization used in the first example easily binds to a thiol compound and remains stable. Accordingly, use of probes each having a thiol group (usually an alkanethiol linker) makes the immobilization easier. In addition, the gold electrode is inactive and is therefore stable in the solution. In other words, the gold electrode does not incur potential drift or the like.

The insulated gate field effect transistor used in the first example is a depletion type FET including an insulating layer made of $SiO_2$ (thickness; 17.5 nm), and the gold electrode is formed in the size of 400 μm×400 μm. Since an aqueous solution is used for a usual measurement, this element has to operate in the solution. In the case of the measurement in the solution, the element is required to operate in an electrode potential range from −0.5 to 0.5 V, where an electrochemical reaction hardly occurs. For this reason, in the first example, a condition for fabricating the depletion type n-channel FET, i.e., an ion implanting condition for adjusting a threshold voltage (Vt) is adjusted to set the threshold voltage of the FET close to −0.5 V.

Figure 3:
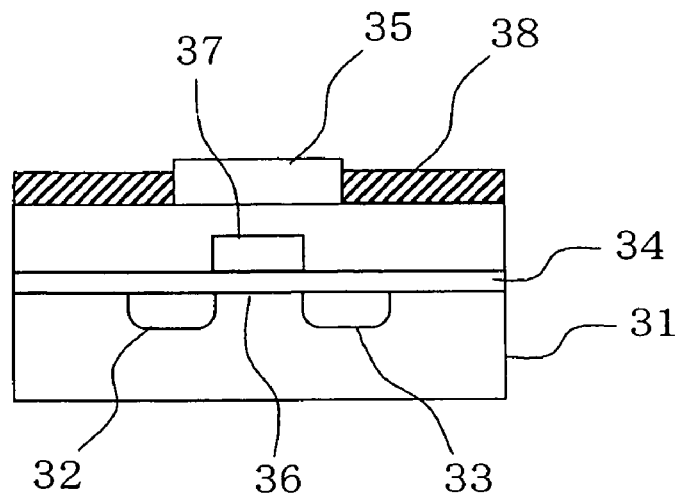
FIG. 3A is a cross sectional view and FIG. 3B is a plain view showing another example of the structure of the insulated gate field effect transistor according to another example of the embodiment of the present invention.
Figure 3:
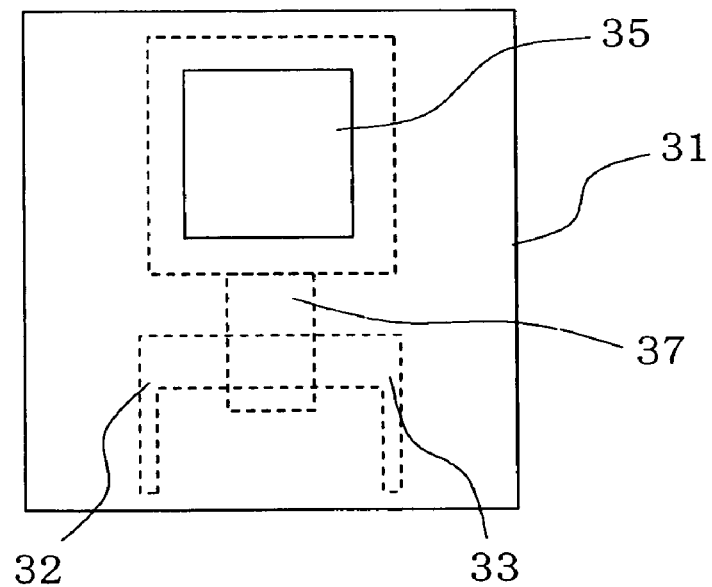

FIGS. 3A and 3B are views showing a structural example of an insulated gate field effect transistor used for a DNA measuring apparatus according to a second example of this embodiment. Here, FIG. 3A shows a cross sectional structure and FIG. 3B shows a plane structure. In an insulated gate field effect transistor, a source 32, a drain 33, and a gate insulator 34 are formed on a surface of a silicon substrate 31, while a gold electrode 35 is also provided thereon. The gold electrode 35 for immobilizing DNA probes is connected to a gate 36 of the insulated gate field effect transistor with a conductive wire 37 interposed in between. The constituents other than the gold electrode are covered with a light-shielding member 38.

Material having a high insulation property and low optical transparency such as plastic material or an adhesive is applicable to the light-shielding member. Alternatively, in the course of the semiconductor fabrication processes, an aluminum layer which is conductive material may be formed. In this case, it is desirable to form an insulating layer between the gold electrode and the aluminum layer and further to connect the aluminum layer to be grounded in order to prevent the aluminum layer from being charged. By adopting this structure, it is possible to easily use the apparatus without requiring a dark box or the like.

Figure 4:
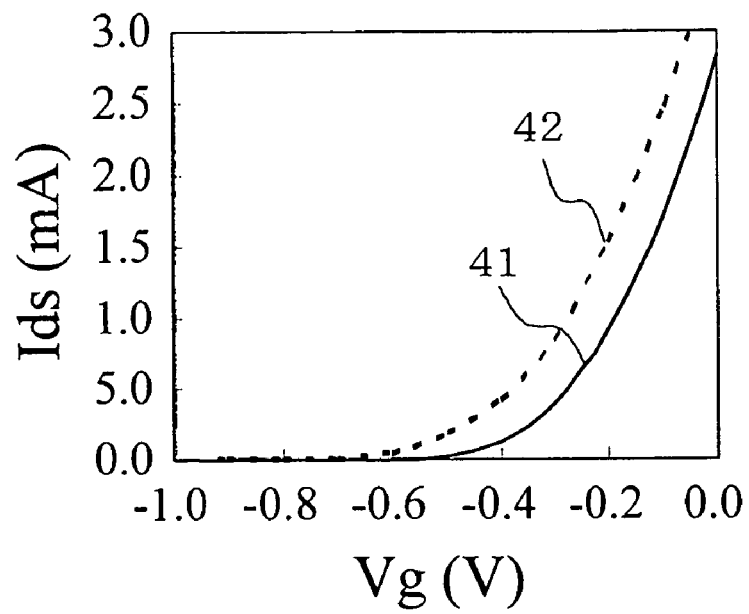
FIGS. 4A and 4B are graphs showing a light-shielding effect of the insulated gate field effect transistor.
Figure 4:
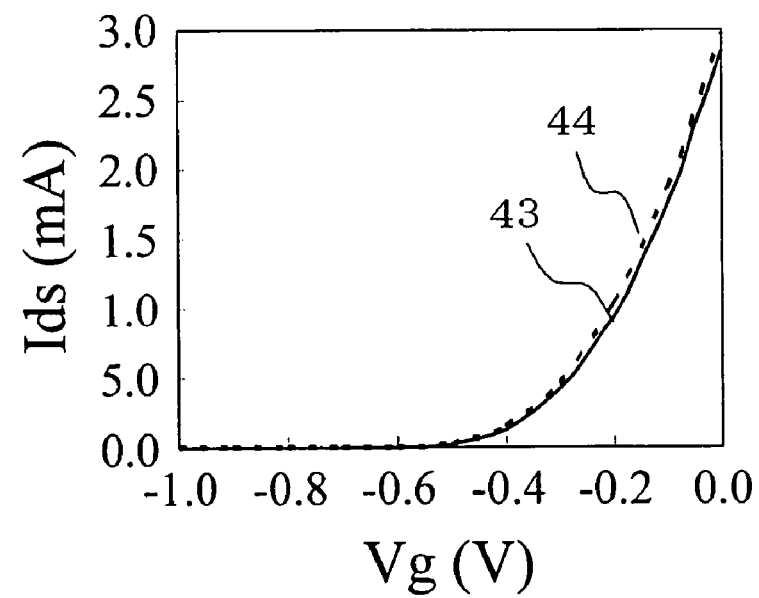

FIGS. 4A and 4B are graphs showing a light-shielding effect of the insulated gate field effect transistor used in the DNA measuring apparatus of the second example. The light-shielding effect is evaluated by comparing measurement results of current and voltage characteristics of the insulated gate field effect transistor with and without a dark box. The current and voltage characteristics of the insulated gate field effect transistor are measured under conditions where a voltage between the source and the drain is 0.5V, where an Ag/AgCl reference electrode is used as a reference electrode, and where a semiconductor parameter analyzer (Agilent 4155C Semiconductor Parameter Analyzer) is used.

FIG. 4A is a graph showing measurement results of the insulated gate field effect transistor not subjected to a light-shielding measure, and FIG. 4B is a graph showing measurement results of an element subjected to the light-shielding measure of covering, with the light-shielding member, the constituents other than the gold electrode which is a sensing area. As shown in FIG. 4A, the insulated gate field effect transistor not subjected to the light-shielding measure exhibits a large variation between a drain current value 41 inside the dark box and a drain current value 42 without the dark box. By contrast, as shown in FIG. 4B, the insulated gate field effect transistor subjected to the light-shielding measure exhibits almost no variation between a drain current value 43 inside the dark box and a drain current value 44 without the dark box. Thus, it is understood that the insulated gate field effect transistor subjected to the light-shielding measure is not affected by light.

Figure 5:
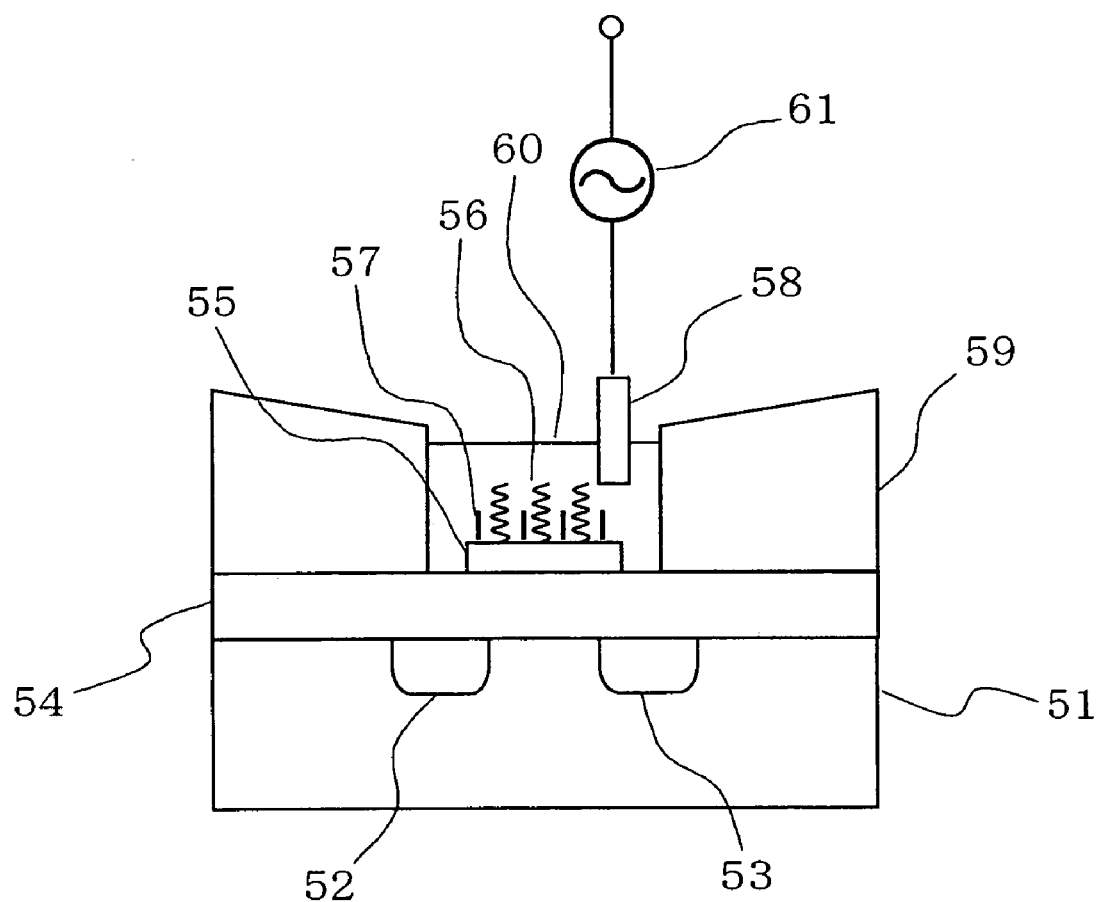
FIG. 5 is a block diagram showing another example of the DNA measuring apparatus according to another embodiment of the present invention.

A second embodiment of the present invention will be described below. FIG. 5 is a view showing a DNA measuring apparatus using a DNA immobilization FET sensor according to this embodiment. In an insulated gate field effect transistor 51 used in this embodiment, a source 52, a drain 53, and a gate insulator 54 are formed on a surface of a silicon substrate, while a gold electrode 55 is provided on a surface of the gate insulator between the source 52 and the drain 53. DNA probes 56 and alkanethiols 57 are immobilized on the surface of the gold electrode 55. In the actual measurement, the gold electrode 55, the DNA probes 56 as well as the alkanethiols 57 immobilized on the surface of the gold electrode 55, and a reference electrode 58 are disposed in a reactive solution 60 inside a measuring cell 59. Then, a high-frequency voltage is applied from a power source 61 to the reference electrode 58 to detect a change in electric characteristics of the insulated gate field effect transistor 51 which change before and after binding of target DNAs with the DNA probes 56 contained in the reactive solution, i.e., a change in a current value between the source 52 and the drain 53. In this way, it is possible to detect the presence or absence of extension of the target DNAs contained in the reactive solution 60.

Hybridization efficiency of DNA largely depends on immobilization density of the DNA probes. For example, when the DNA probes are immobilized in high density, the hybridization efficiency is degraded because the target DNAs to be hybridized cannot approach to the DNA probes, or because adjacent phosphate groups repel each other during formation of a double strand. In addition to the immobilization density, the FET sensor used in this embodiment also has a problem of shielding on the surface of the gold electrode, that is, a problem of removing influences of ions in the solution on the surface of the gold electrode. For this reason, in this embodiment, both of the immobilization density of the DNA probes and immobilization density of the alkanethiol functioning as the linker are considered. Therefore, when the DNA probes 56 are immobilized to the gold electrode 55, the alkanethiols 57 are also immobilized at the same time in order to control a configuration of the DNA probes 56 and to protect the surface of the gold electrode 55.

Figure 6:
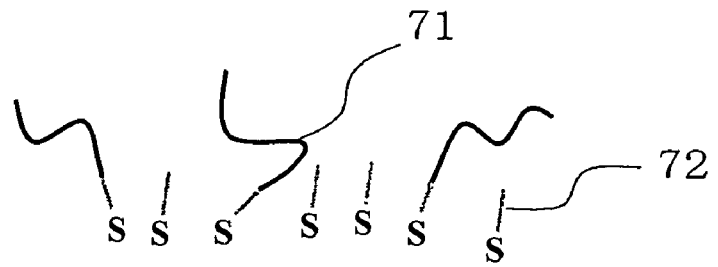
Figure 6:
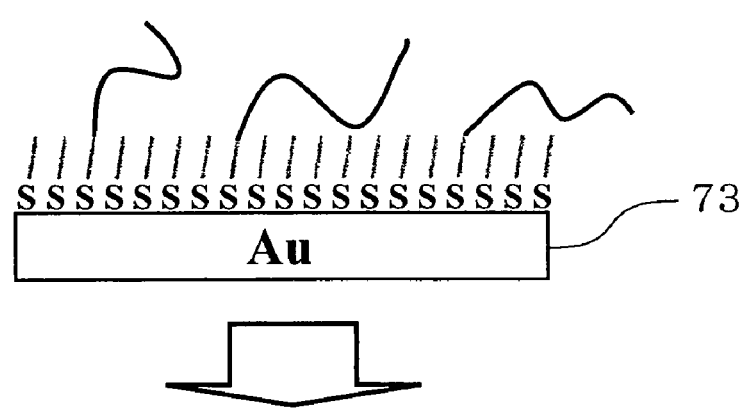
Figure 6:
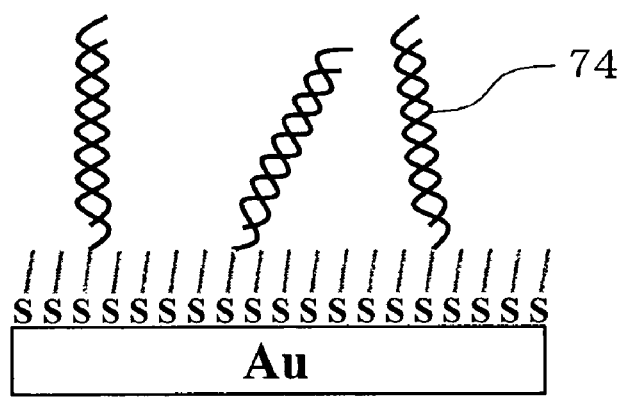

FIGS. 6A to 6C show an operation flow of a method of immobillizing the DNA probes to the gold electrode which is the sensing area of the FET sensor of this embodiment. Here, FIG. 6A is a schematic drawing of a DNA immobilization solution, FIG. 6B is a view showing a state where immobilization density of the DNA probes is controlled, and FIG. 6C is a view showing a state of performing hybridization by use of the DNA probes with the controlled immobilization density.

In general, a compound containing thiol is known to react with a gold surface to form an Au—S bond, thereby forming a self-assembled monolayer film having high density and high orientation. Utilizing this property, this embodiment is configured to cause a competitive reaction between DNA probes 71 and linkers 72, to control immobilization density of the DNA probes, and to shield a surface of a gold electrode 73. A molecule number ratio of the DNA probes to be immobilized to the linkers largely depends on a molecule number ratio of the DNA probes to the linkers in the DNA immobilization solution. Accordingly, it is possible to easily control the immobilization density thereof by changing a mixture ratio of the DNA probe solution to the linker solution. Specifically, it is possible to control the DNA immobilization density and to shield the surface of the gold electrode, easily, by means of only adjusting the mixture ratio of the DNA probes to the linkers prior to the immobilization reaction. Thereafter, it is possible to form double-stranded DNAs 74 by performing hybridization after adding the target DNAs.

The DNA probe immobilization is performed by use of the DNA immobilization solution with a constant molecule number ratio of the DNA probes to the alkanethiol (such as 1:10). As a buffer used therefor, 10 mM Tris-HCl, 5 mM Mg, and pH 7.2 is used. A time for immobilization is set to about one hour. Although the length of the DNA probes used in this embodiment varies depending on the purpose, usually a single-stranded DNA including 20 or more bases is used. Preferably, a single-stranded DNA including 20 to 30 bases is used. Meanwhile, alkanethiol having 6 to 11 carbon chains is typically used as the linker. In the case of immobilizing DNAs, since the DNA is charged negatively, DNA fragments lie down on a surface due to an interaction by using the alkanethiol containing an amino group, and thereby, deteriorating measurement stability (fluctuations of a time for stabilization and of measurement value). Therefore, it is better to use the alkanethiol containing a hydroxyl group or a carboxyl group. The alkanethiol used therefor may be, for example, mercaptoethanol, 6-hydroxy-1-hexanethiol, 8-hydroxy-1-octanethiol, 11-hydroxy-1-undecanethiol and the like, which include a hydroxyl group as an end group. However, there is no problem in using alkanethiol having any of the amino group, the carboxyl group, and the hydroxyl group as the end group in accordance with electric charges in the measurement object. Moreover, in the case of a problem of physical adsorption to the electrode surface, use of alkanethiol having a fluorocarbon group or the like can solve the problem.

The DNA probes used in this embodiment is a single-stranded DNA including the alkanethiol having six carbon chains as the linkers (5'-HS-$(CH_2)_6$-CACACTCA-CAGTTTTCACTT-3', which is a sequence complementary to the ALDH 2 gene). The alkanethiol used for the competitive reaction in this case is 6-hydroxy-1-hexanethiol (6-HHT). The mixture ratio of the DNA probes to 6-HHT is set to be 1:10, and the DNA probe immobilization density is set at $4 \times 10^{12}$ molecules/$cm^2$. Here, the, immobilization density of the DNA probes is obtained by use of CV in a strong alkaline solution. Note that, the more improved is the sensitivity of the FET sensor, the higher is the immobilization density of the DNA probes, Therefore, the immobilization density of the DNA probes is preferably set to be in a range from $4 \times 10^{10}$ molecules/$cm^2$ to $4 \times 10^{12}$ molecules/$cm^2$ in consideration of the ideal immobilization density of the DNA probes. The DNA immobilization solution used therefor contains the DNA probes and the alkanethiol with the molecules number ratios from 1:5 to 1:100. Moreover, it is possible to maintain the shielding effect on the surface of the gold electrode when the concentration of the alkanethiol used for the competitive reaction with the DNA probes is set equal to or above 500 μM.

Figure 7:
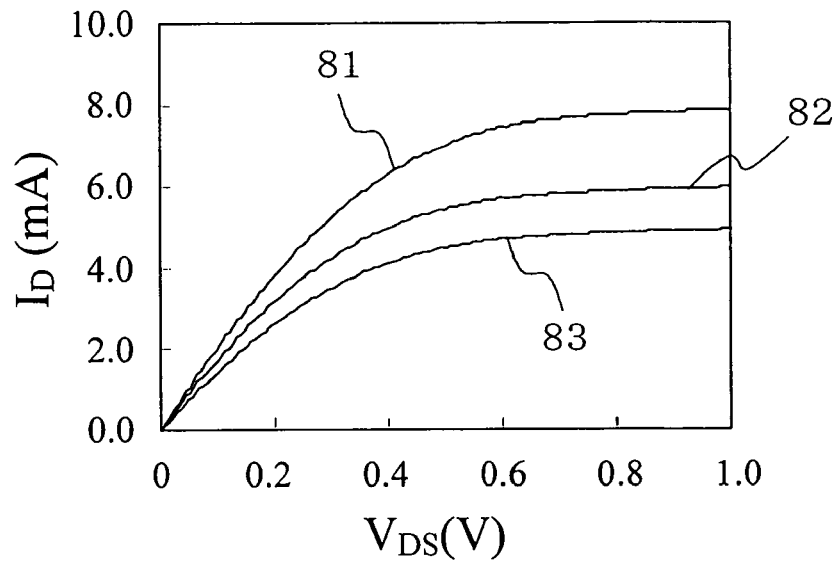
FIG. 7 is a graph showing an example of measurement results of DNA hybridization and extension reactions by use of the DNA measuring apparatus according to the embodiment of the present invention.

Actual measurement results are shown in FIG. 7. The DNA probe immobilization is carried out in a mixture solution with a concentration ratio of the DNA probes to 6-HTT of 1:10. Each of the DNA probes used therefor is a single-strand DNA having 20 bases (5'-HS-$(CH_2)_6$-CACACTCA-CAGTTTTCACTT-3', which is a sequence complementary to the ALDH 2 gene), and each of the target DNAs is a single-strand DNA having 50 bases (5'-TGGGCGAG-TACGGGCTGCAGGCATACACTAAAGT-GAAAACTGTGAG TGTG-3', which is a sequence complementary to the ALDH 2 gene). The measurement is performed by applying, to the reference electrode (the Ag/AgCl reference electrode) at the gate side, an alternating-current voltage of a frequency equal to 1 MHz, a center voltage equal to 50 mV, and an amplitude voltage equal to 50 mV. Reaction conditions and compositions of reagents used in this embodiment are shown below.

Reaction Conditions:
  Reaction volume: 100 μL
  Amount of addition of substrates: 10 μL (dATP, dCTP, dGTP, and dTTP: 200 μM)

Compositions of reagents in a reactive solution:
  0.1 M Tris-acetate buffer, pH 7.75
  0.5 mM EDTA
  5.0 mM magnesium acetate
  0.1% bovine serum albumin
  1.0 mM dithiothreitol
  0.1 U/μL DNA polymerase I, Exo-klenow Fragment A drain current 82 after introduction of the target DNAs (the double-strand DNAs hybridized with the DNA probes) becomes lower than a drain current 81 before the introduction of the reagents (the single-stranded DNAs). Next, when the substrate solution (the mixed solution of dATP, dCTP, dGTP, and dTTP) is added, a drain current 83 becomes even less. The result is considered that a negative charge on the surface of the gold electrode is increased as a consequence of formation of the double-stranded DNA and the extension reaction. In other words, the DNA probes immobilized on the surface of the gold electrode have the phosphate group in a side chain to be negatively charged as a whole. Along with the hybridization, the negative charge is increased by an amount corresponding to the length of the target DNA fragments, and the drain current value is decreased accordingly. Moreover, as a result of the extension reaction, the negative charge is increased by an amount corresponding to the length contributed to extension reaction, and the drain current value is further decreased.

Figure 8:
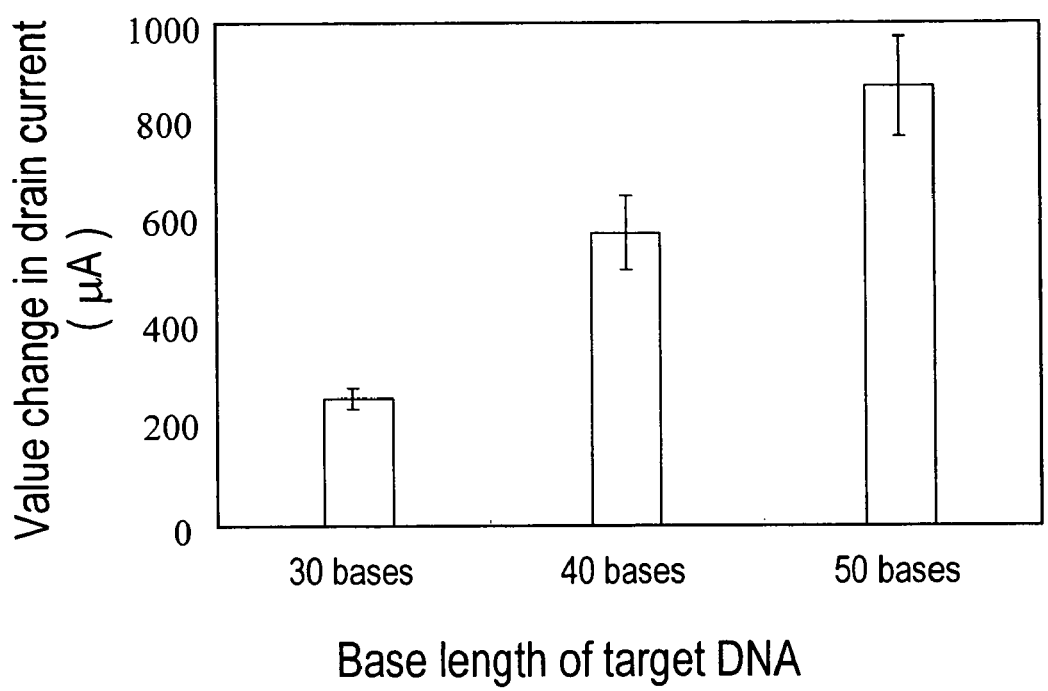
FIG. 8 is a graph showing measurement results of extension reactions of three types of target DNAs having respectively different base lengths.

FIG. 8 shows results of the extension reactions of three different types of target DNAs having respectively different base lengths. Each of the DNA probes used therefor is the single-stranded DNA having 20 bases (5'-HS-(CH2)6-CACACTCACAGTTTTCACTT-3', which is the sequence complementary to the ALDH 2 gene), and the target DNAs include the following three types of single-strand DNAs having 30, 40, and 50 bases, respectively.

The target DNAs:

5'-GCATACACTAAAGTGAAAACTGTGAGTGTG-3'

5'-CGGGCTGCAGGCATACACTAAAGTGAAAACTGTGAGTGTG-3'

5'-TGGGCGAGTACGGGCTGCAGGCATACACTAAAGTGAAAACTGTGAGTGTG-3'

The DNA probe immobilization is performed in the mixed solution with a concentration ratio of the DNA prove to the 6-HHT of 1:10. The measurement is performed, while applying, to the reference electrode (the Ag/AgCl reference electrode) at the gate side, an alternating-current voltage with a frequency of 1 MHz, a center voltage of 50 mV, and an amplitude voltage of 50 mV. As a result, change values in the drain current along with the extension reaction are more increased in descending order of 50 bases, 40 bases, and 30 bases, according to the lengths of the target DNAs (in the cases of the lengths of the target DNAs of 30 bases, 40 bases, and 50 bases, the extension lengths are 10 bases, 20 bases, and 30 bases, respectively). This result shows that the extension reaction in each case causes the negative charge to increase by the amount corresponding to the length contributing to the extension reaction, and that the drain current value changes accordingly.

A sequencing method using the apparatus according to an example of this embodiment will be described below. The principle of the sequencing method to be performed with this apparatus is to detect, as a change in the drain current of the FET sensor, an increase in a phosphate group associated with the extension reaction of the DNA probes hybridized with the target DNAs, i.e., an increase in the negative charge.

The DNA probes which are extension reaction primers are immobilized on the surface of the gold electrode of the FET sensor. The DNA probe immobilization is performed in the mixed solution with a concentration ratio of the DNA prove to the 6-HHT of 1:10. In the measurement, the immobilized DNA probes are hybridized with the target DNAs which are the measurement target, and the extension reaction is produced by adding DNA polymerase in the state of hybridization of the DNA probes with the target DNAs. Here, when different types of deoxyribonucleoside triphosphate, which are substrates for the extension reaction, are sequentially added one by one, the extension reaction occurs only in the case of addition of the deoxyribonucleoside triphosphate with a complementary base. Then, the negative charge is increased along with an increase in the phosphate group, and the drain current thereby changes. This is the method of determining a base sequence one by one, while detecting the presence or absence of the change in the drain current of the FET sensor every time when the different types of deoxyribonucleoside triphosphate are repeatedly and sequentially added one by one. This method can be carried out with the apparatus of this example. For the implement thereof, the excessive unreacted deoxyribonucleoside triphosphate in the reactive solution after the extension reaction may be removed by removing and rinsing off the solution. To be more precise, a series of processes are as follows: one type of the substrates is injected; the presence or absence of the extension reaction is detected after a certain period of time; the reactive solution containing the excessive unreacted deoxyribonucleoside triphosphate is removed and rinsed off; and thereafter, a new reactive solution is added. The series of processes are repeated for each of the four substrates. Alternatively, apyrase which is a decomposing enzyme may be mixed in advance for decomposing the excessive unreacted deoxyribonucleoside triphosphate. This arrangement has an advantage of curtailing the cleaning process. However, the cycle time is extended because the decomposition reaction requires about one minute each time.

Figure 9:
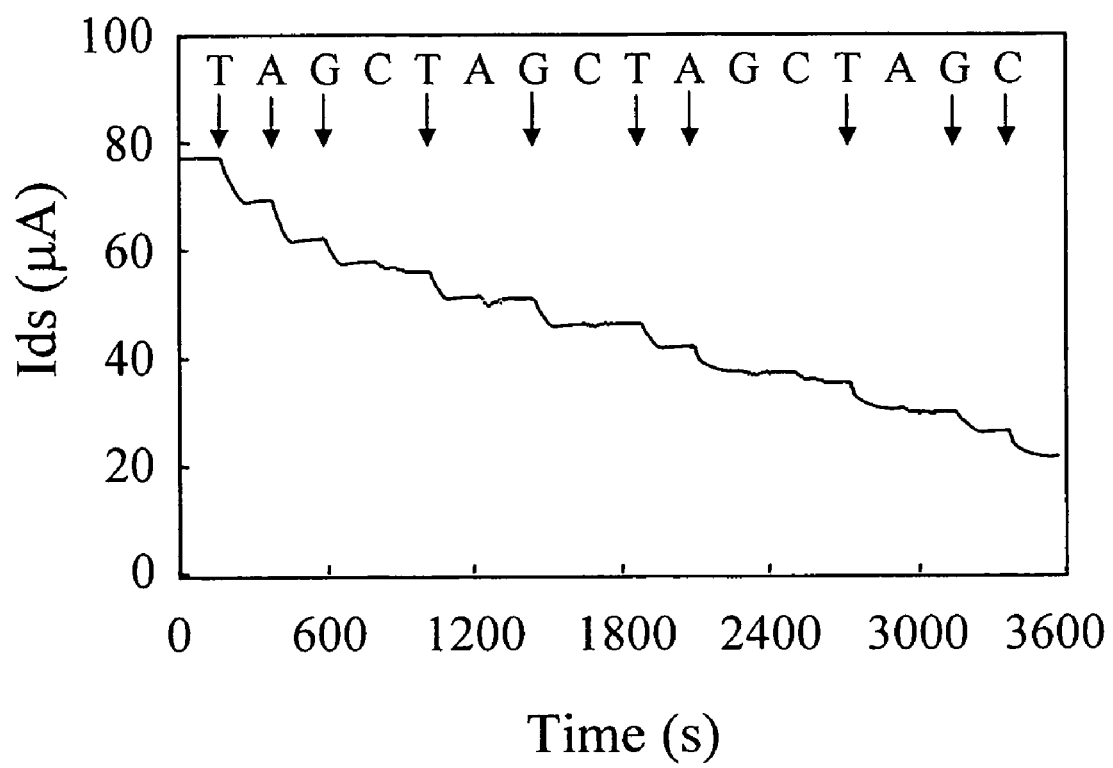
FIG. 9 is a graph showing an example of a result of DNA sequencing by use of the DNA measuring apparatus according to an example of the embodiment of the present invention.

FIG. 9 is a graph showing a result of DNA sequencing using the DNA immobilized FET sensor of this example. The vertical axis of the graph indicates the drain current value of the FET sensor, the lateral axis thereof indicates the time, and reference codes A, C, G, and T indicate the added substances, namely, dATP, dCTP, dGTP, and dTTP. Moreover, arrows which are located below the reference codes A, C, G, and T respectively indicate that the substances thereof include bases complementary to the target DNAs (that is, the matching bases). Each of the DNA probes used therein is a single-stranded DNA having 20 bases (5'-HS-$(CH_2)_6$-CACACTCACAGTTTTCACTT-3', which is a sequence complementary to the ALDH 2 gene). Meanwhile, each of the target DNAs used therein is a single-stranded DNA having 50 bases (5'-TGGGCGAGTACGGGCTGCAGGCATACACTAAAGTGAAAACTGTGAG TGTG-3', which is a sequence complementary to the ALDH 2 gene). Moreover, the DNA probe immobilization is performed in the mixed solution with a concentration ratio of the DNA prove to the 6-HHT of 1:10. The measurement is performed while applying, to the reference electrode (the Ag/AgCl reference electrode) at the gate side, an alternating-current voltage with a frequency of 1 MHz, a center voltage of 50 mV, and an amplitude voltage of 50 mV. Reaction conditions and compositions of reagents used in this example are shown below. Note that the reaction conditions and the concentrations of the reagents used herein merely represent an example of the measuring method, and can be appropriately modified in response to the apparatus configuration or the target DNA.

Reaction Conditions
  Reaction volume: 100 μL
  Amount of addition of substrates: 10 μL (dATP, dCTP, dGTP, and dTTP: 200 μM)

Compositions of Reagents in a Reactive Solution
  0.1 M Tris-acetate buffer, pH7.75
  0.5 mM EDTA
  5.0 mM magnesium acetate
  0.1% bovine serum albumin
  1.0 mM dithiothreitol
  0.1 U/μL DNA polymerase I, Exo-klenow Fragment
  0.1 U/mL Apyrase As a result, it is confirmed that the drain current value decreases only when the complementary bases are added, and that the extension reaction is able to be detected. With data on the types of the added substrates and on the presence or absence of the change in the drain current value in each case, it is possible to determine that the base sequence is ATCACATACG. In this example, the excessive unreacted deoxyribonucleoside triphosphate is removed by mixing apyrase which is the enzyme for decomposing the substrates. Alternatively, it is also possible to remove the excessive unreacted deoxyribonucleoside triphosphate by removing and rinsing off the reactive solution.

Figure 10:
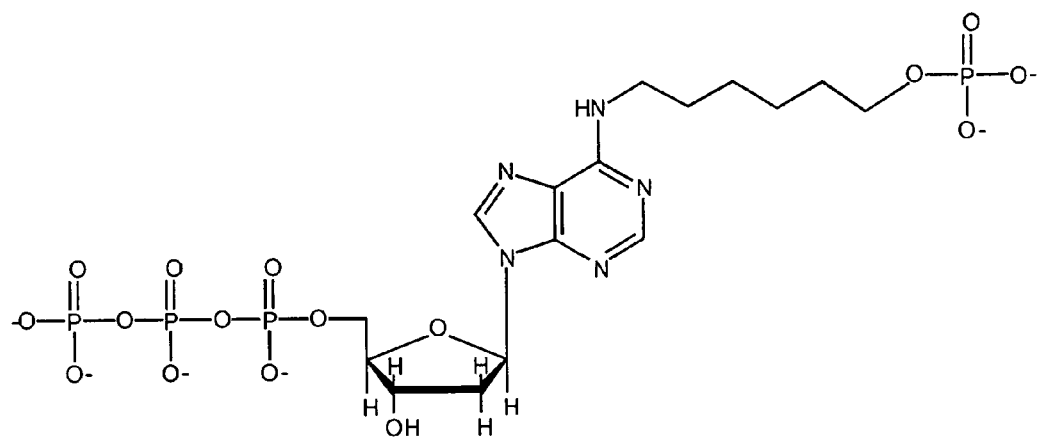
FIGS. 10A and 10B are views showing examples of deoxyribonucleoside triphosphate derivatives.
Figure 10:
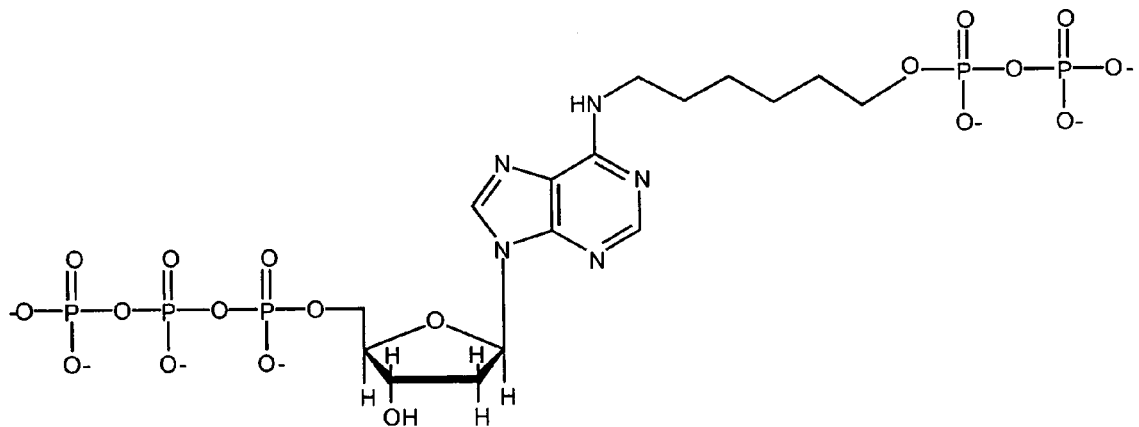

This example uses the deoxyribonucleoside phosphate as the substrate for the sequencing reaction (the extension reaction). However, in order to further enhance the measurement sensitivity, it is possible to use, as the substrate, a derivative in which an additional portion carrying negative charge is bound to a side chain of a constituent base of the deoxyribonucleoside triphosphate. For example, it is possible to use a derivative in which, instead of a fluorescent substance, either a phosphoric acid (FIG. 10A) or a polyphosphoric acid (FIG. 10B) is bound to an amino group of a base with a carbon-chain linker, as similar to a fluorescence-labeled substrate used in general. Although FIGS. 10A and 10B illustrate examples of ATP derivatives, there is also no problem of using GTP, CTP, and TTP derivatives each formed in a manner similar to the fluorescence-labeled substrate. In other words, a fluorescent label for deoxyribonucleoside triphosphate is used, as a dye terminator label, in a sequencing reaction, and thereby, the fluorescent label does not inhibit the sequencing reaction (i.e., the extension reaction), if either the phosphoric acid or the polyphosphoric acid is bonded to the same position by use of a linker with a similar length. Moreover, although in the first example, the specific gene base sequence is used, it is also possible to determine a base sequence of an unknown sample amplified by cloning or PCR as similar to a typical DNA sequencer by using a universal primer (such as the M13 universal primer; 5'-TGTAAAACGACGGCCAGT-3') used in a cloning site, as the case of the typical sequencing.

Figure 11:
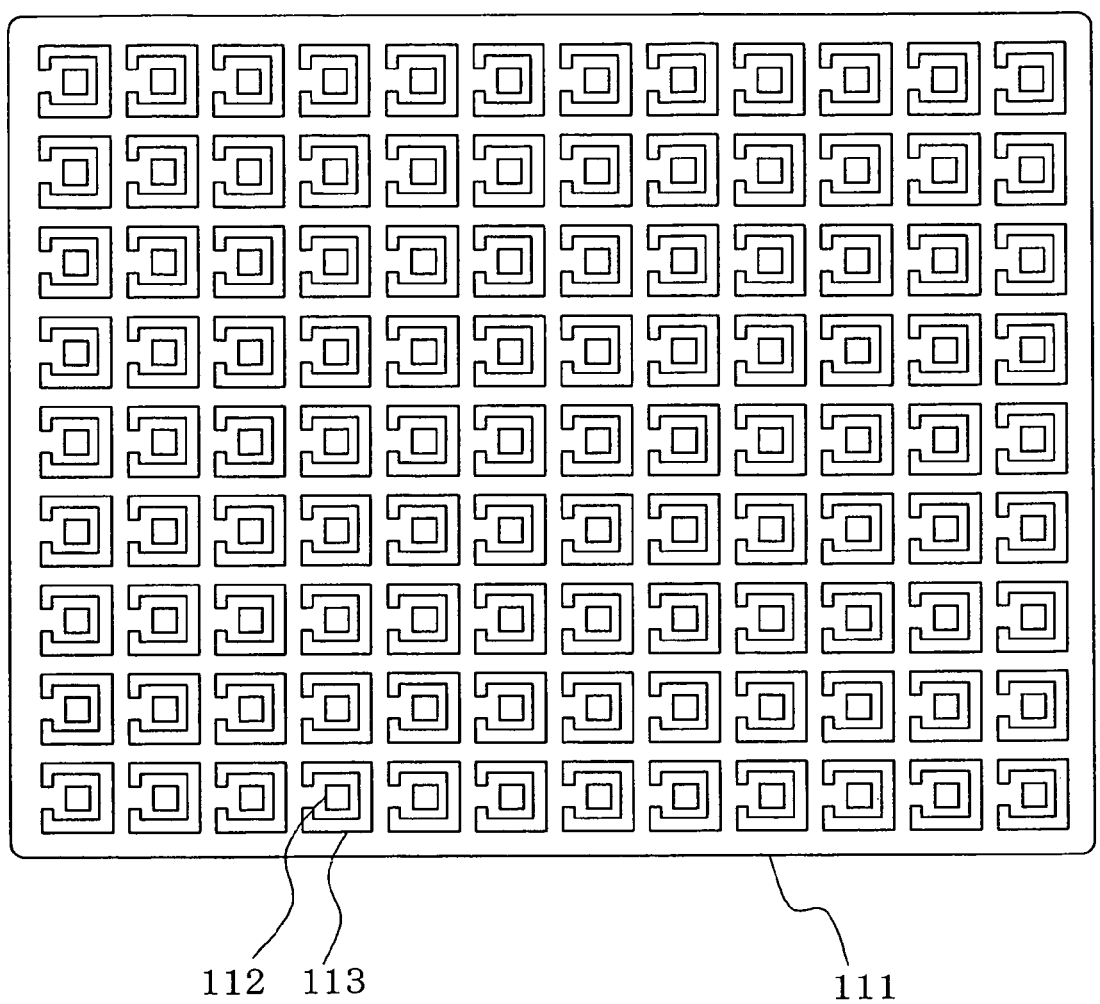
FIG. 11 is a view showing array elements according to another example of the embodiment of the present invention.
Figure 12:
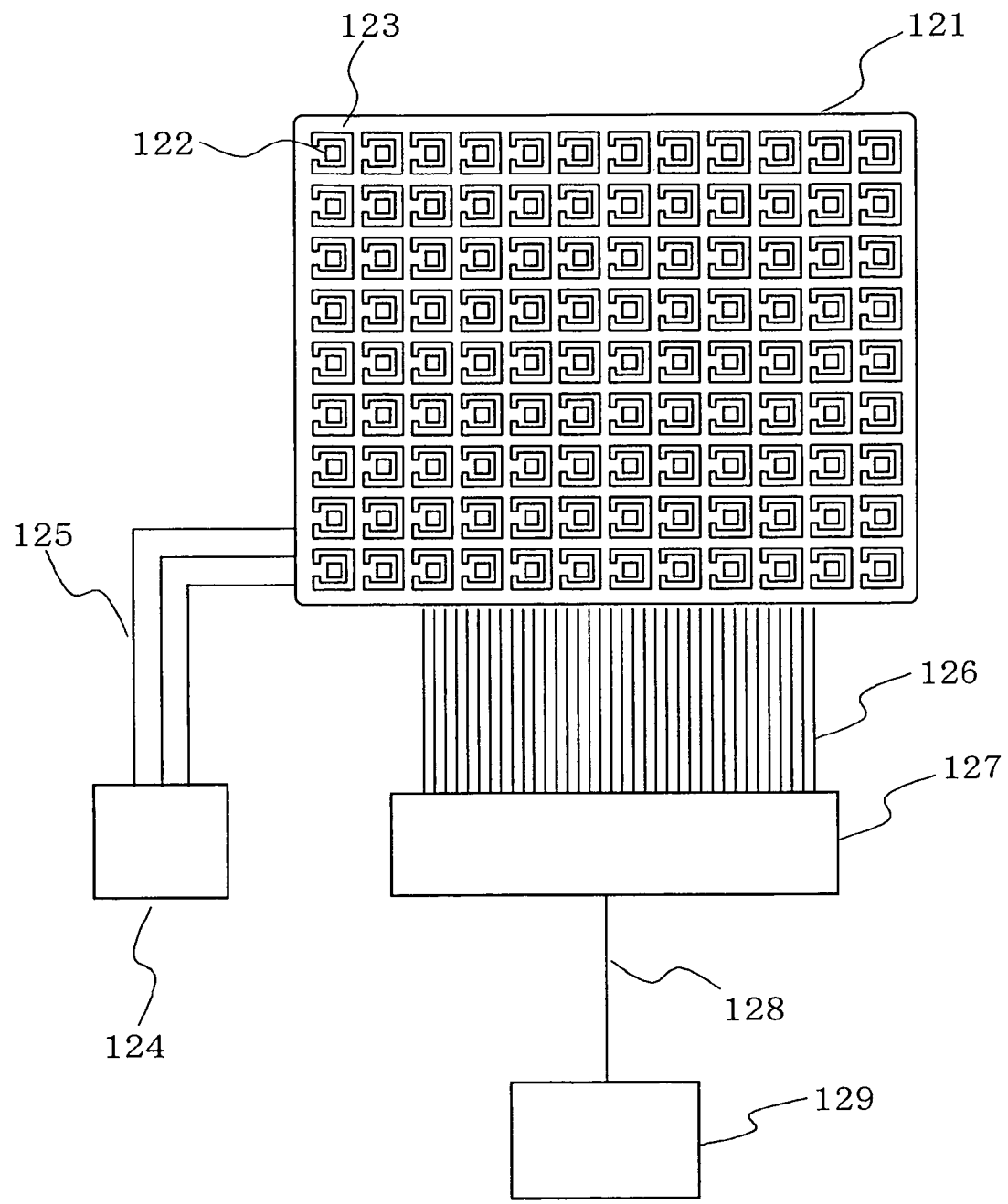
FIG. 12 is a view for explaining a measuring method using the array elements of the example of the embodiment of the present invention.

An example of array elements according to another example of this embodiment of the present invention will be described with reference to FIG. 11. By use of the array elements of this embodiment, a plurality of extended gate transistors are formed on an element substrate 111. On a surface of the substrate, a gate of each of the extended gate transistors is connected to each of gold electrodes 112 with a conductive wire. Each of pseudo reference electrodes 113 is formed so as to surround each of the gold electrodes 112. Even thought immobilization of DNA probes and the alkanethiol on the surface of the gold electrode is insufficient (i.e. a defect exists on the gold electrode), it is made possible to reduce influences, on adjacent elements, such as current generation and a potential gradient on the surface of gold at an exposed portion caused by the defect. Moreover, by forming the plurality of transistors on the single substrate, there is also an advantage to equalize electric characteristics among the transistors. In the actual measurement by use of the array elements, the needed number of both power supply lines for input for the transistors and output lines for signals is the same number as the array elements. Therefore, in the example of this embodiment, as shown in FIG. 12, in the case of using array elements each including a pair of a gold electrode 121 connected to a gate of each extended gate transistor with the conductive wire, and a pseudo-electrode 123 surrounding the gold electrode 121, input lines from a power source 124 to the respective transistors are configured to form a common line. Meanwhile, one of outputted signals from the respective transistors through signal output lines 126 is selected by a multiplexer 27, and then, is inputted to a signal processing device 129 through a signal output line 128. Thereby, the number of input and output lines is decreased. In addition, In addition, it is possible to further reduce the number of lines by integrally forming the signal output lines 126 and the multiplexer 127 on the array element substrate 121. This array element is a metal-oxide-semiconductor field effect transistor (FET) using a silicon oxide as an insulating film. However, it is also possible to use a thin-fill transistor (TFT) in this case.

What is claimed is:

1. A method of measuring DNAs comprising the steps of:
   contacting a gold electrode of a field effect transistor with a measurement solution containing DNA polymerase, DNA probes are immobilized on a surface of the gold electrode, wherein the gold electrode is connected to a gate of the field effect transistor with a conductive wire;
   applying a high-frequency voltage having a frequency greater than or equal to 1 kHz and at a constant amplitude, between the gold electrode and a reference electrode contacting with the measurement solution;
   injecting sample DNAs into the measurement solution thereby binding the sample DNAs to the DNA probes;
   injecting into the measurement solution at least one type of deoxyribonucleoside triphosphate selected from a group consisting of dATP, dCTP, dGTP, and dTTP, or at least one type of deoxyribonucleoside triphosphate derivatives after finishing the step of injecting sample DNAs for a predetermined period of time, thereby enzymatically extending the DNA probes;
   measuring an electric characteristic change of the transistor either before and after binding the sample DNAs to the DNA probes, or before and after extension of the DNA probes; and
   detecting any of presence/absence of the sample DNAs bound to the DNA probes, based upon the measured electric characteristic change of the transistor.

2. The method of measuring DNAs according to claim 1, further comprising:
   adding into the measurement solution a deoxyribonucleoside triphosphate decomposing enzyme after extension of the DNA probes; and
   detecting a base sequence of each of the sample DNAs complementary to said one type of deoxyribonucleoside triphosphate and corresponding to the decomposing enzyme based upon the measured electric characteristic change of the field effect transistor before and after extension of the DNA probes,
   wherein only one type of the deoxyribonucleoside triphosphate, or only one type of the deoxyribonucleoside triphosphate derivatives corresponding to the decomposing enzyme is injected into the measurement solution.

3. The method of measuring DNAs according to claim 2, wherein the step of injecting only one type of the deoxyribonucleoside triphosphate or only one type of the deoxyribonucleoside triphosphate derivatives, the step of detecting a base sequence, and the step of adding the decomposing enzyme are repeated for each of the four types of deoxyribonucleoside triphosphate.

4. The method of measuring DNAs according to claim 1, wherein the DNA probes are immobilized on the surface of the gold electrode with alkanethiol binding to one end of each of the DNA probes.

5. The method of measuring DNAs according to claim 1, wherein when a deoxyribonucleoside triphosphate derivative is used, the deoxyribonucleoside triphosphate derivative is a derivative of a corresponding deoxyribonucleoside triphosphate including an additional portion carrying a negative charge which is bound to a side chain of a constituent base.

6. The method of measuring DNAs according to claim 5, wherein a part of the additional portion includes a phosphate group.

7. The method of measuring DNAs according to claim 1, wherein the DNA probes have a base sequence of a universal primer used for sequencing.

8. The method of measuring DNAs according to claim 1, wherein at least one of (1) a voltage between a source and a drain and (2) a gate voltage change is measured either before and after binding the sample DNAs to the DNA probes or before and after extension of the DNA probes while maintaining a drain current at a constant level.

9. The method of measuring DNAs according to claim 1, wherein the electric characteristic change of the transistor is a current change between a source and a drain of the transistor.

10. The method of measuring DNAs according to claim 1, wherein alkanethiol is fixed on the surface of the gold electrode together with the DNA probes to optimize immobilization density of the DNA probes on the gold electrode.

11. The method of measuring DNAs according to claim 10, wherein a molecule number ratio of the DNA probes to the alkanethiol is in a range of 1:2 to 1:100.

12. A method of sequencing a sample DNA comprising:
contacting a gold electrode of a field effect transistor with a measurement solution containing DNA polymerase, DNA probes are immobilized on a surface of the gold electrode, wherein the gold electrode is connected to a gate of the field effect transistor with a conductive wire;
applying a high-frequency voltage between the gold electrode and a reference electrode contacting with the measurement solution;
injecting a plurality of the sample DNAs into the measurement solution thereby binding the sample DNAs to the DNA probes;
repeating steps (1)-(4) sequentially for each type of a deoxyribonucleoside triphosphate selected from a group consisting of dATP, dCTP, dGTP, and dTTP, or a deoxyribonucleoside triphosphate derivatives after finishing the step of injecting sample DNAs for a predetermined period of time:
(1) injecting into the measurement solution only one type of the deoxyribonucleoside triphosphate or only one type of the deoxyribonucleoside triphosphate derivatives, thereby enzymatically extending the DNA probes;
(2) measuring an electric characteristic change of the transistor before and after extension of the DNA probes;
(3) detecting positions of a base sequence on the sample DNA complementary to said one type of deoxyribonucleoside triphosphate, based upon the measured electric characteristic change of the field effect transistor before and after extension of the DNA probes; and
(4) removing or rinsing off excessive said one type of deoxyribonucleoside triphosphate or deoxyribonucleoside triphosphate derivative.

13. A method of sequencing a sample DNA according to claim 12, wherein the removing step is conducted with a deoxyribonucleoside triphosphate decomposing enzyme.

14. A method of sequencing a sample DNA according to claim 12, wherein only when a complementary type of base is added, the extension reaction is detected via a decrease of a drain current value.

* * * * *